(12) United States Patent
Manikandan et al.

(10) Patent No.: US 8,816,130 B2
(45) Date of Patent: Aug. 26, 2014

(54) HETEROGENEOUS CATALYST AND ITS USE

(75) Inventors: Palanichamy Manikandan, Pune (IN); Sreenivasa Rao, Pune (IN); Phani Kiran Bollapragada, Pune (IN); David G. Barton, Midland, MI (US); Richard M. Wehmeyer, Lake Jackson, TX (US); William Tenn, Houston, TX (US); Gerolamo Budroni, Terneuzen (NL)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/977,113

(22) PCT Filed: Jan. 12, 2012

(86) PCT No.: PCT/US2012/021015
§ 371 (c)(1),
(2), (4) Date: Jun. 28, 2013

(87) PCT Pub. No.: WO2012/108973
PCT Pub. Date: Aug. 16, 2012

(65) Prior Publication Data
US 2013/0310610 A1    Nov. 21, 2013

Related U.S. Application Data

(60) Provisional application No. 61/441,679, filed on Feb. 11, 2011.

(51) Int. Cl.
| | |
|---|---|
| *C07C 45/50* | (2006.01) |
| *C07C 29/16* | (2006.01) |
| *B01J 23/89* | (2006.01) |
| *B01J 27/24* | (2006.01) |
| *B01J 21/00* | (2006.01) |
| *C07C 47/02* | (2006.01) |
| *C07C 29/17* | (2006.01) |
| *B01J 23/00* | (2006.01) |
| *B01J 37/02* | (2006.01) |
| *B01J 21/08* | (2006.01) |
| *B01J 21/10* | (2006.01) |
| *B01J 35/10* | (2006.01) |
| *B01J 21/06* | (2006.01) |

(52) U.S. Cl.
CPC .............. *B01J 27/24* (2013.01); *B01J 23/8946* (2013.01); *B01J 23/8993* (2013.01); *C07C 47/02* (2013.01); *B01J 23/898* (2013.01); *C07C 29/16* (2013.01); *B01J 21/08* (2013.01); *B01J 21/10* (2013.01); *C07C 29/172* (2013.01); *B01J 23/8986* (2013.01); *B01J 23/002* (2013.01); *B01J 23/8953* (2013.01); *B01J 35/1014* (2013.01); *B01J 2523/00* (2013.01); *B01J 37/0201* (2013.01); *B01J 21/005* (2013.01); *C07C 45/50* (2013.01); *B01J 21/063* (2013.01)
USPC ........... 568/451; 568/896; 502/183; 502/184; 502/252; 502/329

(58) Field of Classification Search
USPC ........... 568/451, 896; 502/183, 184, 252, 329
See application file for complete search history.

(56) References Cited

U.S. PATENT DOCUMENTS

| 4,361,711 A | 11/1982 | Blaskie et al. |
| 4,492,773 A | 1/1985 | Ball et al. |

OTHER PUBLICATIONS

Sachter and Ichikawa. Catalytic Site Requirements for Elementary Steps in Syngas Conversion to Oxygenates over Promoted Rhodium, J. Phys. Chem., 1986, 4752-4758, 90(20).
PCT/US2012021015 International Search Report and Written Opinion of the International Searching Authority, Mar. 19, 2012.
PCT/ US2012021015 International Preliminary Report on Patentability May 31, 2013.
PCT/ US2010/021015 Written Opinion of the International Preliminary Examining Authority, Feb. 26, 2013.
PCT/ US2010/021015 Response Written Opinion, Nov. 9, 2012.
PCT/ US2010/021015 Response Written Opinion, Apr. 23, 2013.

*Primary Examiner* — Sikarl Witherspoon

(57) ABSTRACT

A heterogeneous catalyst that is a combination of rhodium, zinc, iron, a fourth metal and at least one metal selected from alkali metals and alkaline earth metals on a catalyst support (e.g. at least one of silica, alumina, titania, magnesia, zinc aluminate ($ZnAl_2O_4$), magnesium aluminate ($MgAl_2O_4$), magnesia-modified alumina, zinc oxide-modified alumina, zirconium oxide-modified alumina, and zinc oxide) and use of the catalyst in converting an alkylene to an oxygenate that has one more carbon atom than the alkylene.

6 Claims, No Drawings

HETEROGENEOUS CATALYST AND ITS USE

This application is a non-provisional application claiming priority from the U.S. Provisional Patent Application No. 61/441,679, filed on Feb. 11, 2011, entitled "HETEROGENEOUS CATALYST AND ITS USE" the teachings of which are incorporated by reference herein, as if reproduced in full hereinbelow.

This invention relates to a heterogeneous catalyst that comprises a promoted combination of rhodium (Rh), zinc (Zn), iron (Fe) and at least one additional metal selected from a group consisting of gold (Au), cerium (Ce), cobalt (Co), copper (Cu), lanthanum (La), chromium (Cr), manganese (Mn), niobium (Nb), an alkali metal and an alkaline earth metal on a catalyst support and to use of such heterogeneous catalyst in converting a feedstream of an alkylene (e.g. ethylene) and synthesis gas ("syngas", a mixture of carbon monoxide (CO) and hydrogen ($H_2$)) to a product stream that comprises an oxygenate that has one carbon atom more than the alkylene in the feedstream (i.e. at least one three carbon ($C_3$) oxygenate (e.g. propionaldehyde or propanol) when the alkylene is ethylene).

U.S. Pat. No. 4,361,711 (Blaskie et al.) discloses a single step process to catalytically convert a mixture of an olefin (18 carbon atoms ($C_{18}$) or less), CO and $H_2$ to alcohols using a Rh catalyst. The catalyst, represented by formula $A_a RhO_x$, is a Rh-containing oxide complex that comprises at least one additional element (A) selected from Fe, Zn, iridium (Ir), ruthenium (Ru), Nb, Cr, Mn and platinum (Pt). In the formula, a is 0.001 to 10 and x is greater than 0, but less than a number sufficient to satisfy the valence requirements of the other elements present when in a fully oxidized state. For preferred catalysts A is Zn, Fe and/or Mn and a is 0.6 to 2.0. The oxide complexes, when in use, are in a reduced state such that they contain less oxygen than necessary to satisfy all of the valence requirements of the metals present in a fully oxidized state. The oxide complexes may be used neat, but are preferably disposed on a conventional catalyst support material such as silica, alumina, zirconia, kieselguhr, titania and molecular sieves.

W. M. H. Sachtler et al., in "Catalytic Site Requirements for Elementary Steps in Syngas Conversion to Oxygenates over Promoted Rhodium", *Journal of Physical Chemistry*, volume 90 (1986), pages 4752-4758, presents information on effects of various promoter metals that modify performance of a Rh-containing catalyst in synthesis (syngas) conversion. The promoter metals include Mn, zirconium (Zr), titanium (Ti), vanadium (V) and Nb. Catalyst supports include oxides of Zn, magnesium (Mg), calcium (Ca), La, neodymium (Nd), Zr, Ti, Nb, Mn, silicon (Si) and aluminum (Al).

U.S. Pat. No. 4,492,773 (Ball et al.) teaches production of one to four carbon ($C_1$ to $C_4$) oxygenates by contacting syngas at a temperature within a range of 150 degrees Celsius (° C.) to 450° C. and a pressure within a range of from 1 bar (100 kilopascals (KPa) to 700 bars (70,000 KPa) with a catalyst comprising a supported mixture of a Rh component and a silver (Ag) component. Other metal components that may be incorporated include Fe, Mn, molybdenum (Mo), tungsten (W), Ru, Cr, thorium (Th) and Zr. Support materials include silica, alumina, silica/alumina, magnesia, thoria, titania, chromia, zirconia, and active carbon, with silica ($SiO_2$) being preferred.

In some aspects, this invention is a heterogeneous catalyst consisting essentially of a combination of rhodium, zinc, iron, a fourth metal and at least one metal selected from alkali metals and alkaline earth metals on a catalyst support, the combination of metals being represented by general formula $Rh_a Zn_b Fe_c X_d Y_e O_f$ wherein X is at least one fourth metal selected from a group consisting of Au, Ce, Co, Cu, La, Cr, Mn and Nb, Y is at least one of an alkali metal and an alkaline earth metal, a is a real number within a range of from 0.1 millimole per hectogram (mmol/hg to 50 mmol/hg, b is a real number within a range of from 0.1 mmol/hg to 75 mmol/hg, c is a real number within a range of from 0.1 mmol/hg to 100 mmol/hg, d is a real number within a range of from greater than or equal to 0 mmol/hg to 50 mmol/hg, e is a real number within a range of from greater than or equal to 0 mmol/hg to 1500 mmol/hg, and f is a real number needed to balance the total charges of Rh, Zn, Fe, X and Y elements, provided that provided that d and e cannot both be 0 and when d is greater than 0 and X is at least one of Cr, Mn and Nb, e is also greater than 0, the catalyst support being at least one of silica, alumina, titania, magnesia, zinc aluminate ($ZnAl_2O_4$), magnesium aluminate ($MgAl_2O_4$), magnesia-modified alumina, zinc oxide-modified alumina, zirconium oxide-modified alumina, and zinc oxide. In some aspects, at least one of the metals is in a partially reduced state such that f is greater than 0, but less than a number sufficient to satisfy the valence requirements of the other elements present when in a fully oxidized state.

In some aspects, the heterogeneous catalyst is admixed with an amount of an alkali metal carbonate or alkaline earth metal carbonate. The amount of alkali metal carbonate or alkaline earth metal carbonate, preferably alkali metal carbonate, is preferably within a range of from greater than 0.1 mmol/hg to 75 mmol/hg based upon combined weight of the heterogeneous catalyst and the alkali metal carbonate. The alkali metal carbonate is preferably selected from sodium carbonate and lithium carbonate.

In some aspects, this invention is a process of converting a feedstream comprising a mixture of CO, $H_2$ and alkylene (e.g. ethylene, propylene, butylene, pentene, hexene, heptene or octene) to a product stream that comprises at least one oxygenate that has one more carbon atom than the alkylene in the feedstream (e.g. a three carbon oxygenate when the alkylene is ethylene), which process comprises placing the feedstream in contact with the heterogeneous catalyst or the admixture of the heterogeneous catalyst and an alkali metal carbonate under conditions sufficient to effect conversion of the feedstream to the product stream, said conditions including a temperature within a range of from 100° C. TO 450° C., a pressure within a range of from 12 pounds per square inch gauge (psig) (82.7 kilopascals (KPa)) to 4,000 psig (27.6 megapascals (MPa)), a gas hourly space velocity (GHSV) within a range of from 25 reciprocal hours ($h^{-1}$) to 25,000 $h^{-1}$, and a feedstream ratio of alkylene to CO to $H_2$ ($C_2H_4$:CO:$H_2$) within a range of from 0.01:10:10 to 10.0:0.01:0.01. The feedstream may also contain other components like methane, nitrogen, carbon dioxide, acetylene, hydrogen sulfide, sulfur dioxide, alkanes (e.g. ethane or propane). The feedstream may be a mixture of more than one alkylenes (e.g. ethylene and propylene).

The heterogeneous catalyst disclosed herein and represented by general formula $Rh_a Zn_b Fe_c X_d Y_e O_f$ consists essentially of a combination of Rh, Zn, Fe, a fourth metal (X) and at least one metal (Y) selected from alkali metals and alkaline earth metals on a catalyst support. X is at least one metal selected from a group consisting of Au, Ce, Co, Cu, La, Cr, Mn and Nb. Y is at least one of an alkali metal and an alkaline earth metal. In the formula, a is a real number within a range of from 0.1 mmol/hg to 50 mmol/hg, b is a real number within a range of from 0.1 mmol/hg to 75 mmol/hg, c is a real number within a range of from 0.1 mmol/hg to 100 mmol/hg, d is a real number within a range of from greater than or equal to 0 mmol/hg to 50 mmol/hg, e is a real number within a range of from greater than or equal to 0 mmol/hg to 1500 mmol/hg, and f is a real number needed to balance the total charges of Rh, Zn, Fe, X and Y elements. In the formula, d and e cannot both be 0 and e must be greater than 0 when X is at least one of Cr, Mn and Nb. The catalyst support is at least one of silica, alumina, titania, magnesia, zinc aluminate ($ZnAl_2O_4$), magnesium aluminate ($MgAl_2O_4$), magnesia-modified alumina, zinc oxide-modified alumina, zirconium oxide-modified alumina, and zinc oxide. Silica, magnesia, magnesium aluminate and alumina constitute preferred supports.

In the process of converting a feedstream comprising a mixture of CO, $H_2$ and alkylene to a product stream that comprises at least one oxygenate that has one carbon more than the alkylene in the feedstream, place the feedstream in contact with the heterogeneous catalyst or the admixture of the heterogeneous catalyst and an alkali metal carbonate or alkaline earth metal carbonate under conditions sufficient to effect conversion of the feedstream to the product stream. The conditions include a temperature within a range of from 100° C. TO 450° C., a pressure within a range of from 12 psig (82.7 KPa) to 4,000 psig (27.6 MPa), a gas hourly space velocity (GHSV) within a range of from 25 $h^{-1}$ to 25,000 $h^{-1}$, and a feedstream ratio of alkylene ($C_nH_{2n}$, where n is an integer within a range of from 2 to 8) to CO to $H_2$ ($C_nH_{2n}$:CO:$H_2$) within a range of from 0.01:10:10 to 10.0:0.01:0.01.

The alkali metals include sodium (Na), lithium (Li), potassium (K), rubidium (Rb), cesium (Cs) and francium (Fr). The alkaline earth metals include magnesium (Mg), beryllium (Be), calcium (Ca), strontium (Sr), barium (B a) and radium (Ra). When the catalyst includes component Y, one may use at least alkali metal, or at least one alkaline earth metal or a combination of at least one alkali metal and at least one alkaline earth metal.

One may admix an alkali metal carbonate such as sodium carbonate with catalyst compositions represented by the above general formula. The alkali metal carbonate appears to reduce catalyst acidity, a possible explanation for a reduced tendency to promote hydrogenation of alkenes to alkenes during the process of at least some aspects of this invention.

The process of at least some aspects of this invention has utility in producing at least one oxygenate (e.g. a $C_3$ oxygenate). The oxygenates, in turn have utility in serving as feedstocks for production of other chemicals such as production of propylene by dehydration of the $C_3$ oxygenate propanol. Propylene, in turn, has utility as a feedstock in making a variety of polymeric materials such as polypropylene that finds a number of uses in fabricated articles.

The heterogeneous catalysts provide an ethylene conversion of more than 10 mole percent (mol %), based upon total moles of alkylene (e.g. ethylene) in the feedstream, and a selectivity to oxygenates (e.g. $C_3$ oxygenates when the alkylene is ethylene, preferably to propanol and propanal (propionaldehyde)) of at least 30 mol % based upon total moles of product in the product stream. Selectivity to $C_3$ oxygenates preferably favors propanol over propanal such that the product stream contains more propanol than propanal.

Arabic numerals designate Examples (Ex) of the present invention and capital alphabetic letters indicate Comparative Examples (Comp Ex or CEx).

CEx A

In a 50 ml round bottom flask equipped with a stirring bar, add an aqueous solution containing 0.0128 gram (g) rhodium chloride trihydrate ($RhCl_3.3H_2O$) (Hindustan Platinum India Limited) and 0.0018 g sodium nitrate ($NaNO_3$) (S.D. Fine) dissolved in 12.5 milliliters (ml) of distilled water to 0.5 g of silica (Aerosil™ 300, Degussa, surface area=300±30 square meters per gram ($m^2/g$)) with constant stirring at room temperature (nominally 25° C.) for an hour. Subject container contents to drying first under vacuum at 80° C. for 1 hr and then at 120° C. for 4 hours (hrs). Calcine dried container contents in air at 400° C. for 4 hrs to yield a silica-supported Rh catalyst. The catalyst is represented as $Rh_1Na_{0.1}/SiO_2$ (Rh: 9.7 mmol/hg; Na: 4.3 mmol/hg)

Evaluate catalyst performance using a high pressure parallel fixed bed reactor (PFBR) (PFBR System P/N; 132603 from Symyx™ Technologies Inc), a modular reactor composed of three bays, each of which contains 16 reactor tubes. The tubes in each bay are enclosed in a stainless steel bell jar capable of being pressurized with nitrogen ($N_2$) at the same pressure as that used in each reaction. Load reactor tubes with 200 microliters (μL) of catalyst, reduce the catalyst in situ at 35 bar (3.5 megapascals (MPa)) for three hours at 350° C. (heating rate of 5° C. per minute) using a gaseous mixture of 90 volume percent (vol %) hydrogen ($H_2$) and 10 vol % $N_2$, each vol % being based on total gaseous mixture volume. Cool the catalyst to 280° C.

Test the catalyst at a pressure of 35 bar (3.5 MPa), temperatures of 280° C., 300° C. and 320° C. and GHSV of 6744 reciprocal hours ($hr^{-1}$) using a feed mixture of 42.6 vol % $H_2$, 42.6 vol % CO, 4.8 vol % ethylene and 10 vol % $N_2$, each vol % being based on total feed mixture volume. Continue testing at 320° C. but at a pressure of 90 bar (9 MPa), then return the pressure to 35 bar (3.5 MPa) and test at 340° C. Evaluate reactor tube effluent using a Siemens process GC. Replicate this catalyst test cycle two additional times and report test results as an average of three test cycles in Table 1 below.

CEx B

Replicate CEx A with changes. First, eliminate $RhCl_3.3H_2O$. Second, add 0.0045 g of $Zn(NO_3)_2.6H_2O$ (S. D. Fine) and 0.0049 g of $Co(NO_3)_2.6H_2O$ (S. D. Fine). Third, use a mortar and pestle to physically mix such catalyst with 0.0025 g of sodium carbonate ($Na_2CO_3$ also referred to herein as "NC") to yield a catalyst sample suitable for testing. The catalyst is represented as $Zn_{0.2}Co_{0.2}Na_{0.1}$—$NC_{0.5}/SiO_2$. (Zn: 3.1 mmol/hg; Co: 3.4 mmol/hg; Na: 4.3 mmol/hg; NC: 4.7 mmol/hg).

EX 1

Replicate CEx B but add 0.0128 g $RhCl_3.3H_2O$ (Hindustan Platinum India Limited), and substitute 0.0052 g of $Fe(NO_3)_2.6H_2O$ (S. D. Fine) for $Co(NO_3)_2.6H_2O$ The catalyst is represented as $Rh_1Zn_{0.2}Fe_{0.2}Na_{0.1}$—$NC_{0.5}/SiO_2$. (Rh: 9.7 mmol/hg; Zn: 3.1 mmol/hg; Fe: 3.6 mmol/hg; Na: 4.3 mmol/hg; NC: 4.7 mmol/hg).

EX 2

Replicate Ex 1, but add 0.0017 g of $HAuCl_4.3H_2O$ (Acros). The catalyst is represented as $Rh_1Zn_{0.2}Fe_{0.2}Au_{0.2}Na_{0.1}$—$NC_{0.5}/SiO_2$. (Rh: 9.7 mmol/hg; Zn: 3.1 mmol/hg; Fe: 3.6 mmol/hg; Au: 1.0 mmol/hg; Na: 4.3 mmol/hg; NC: 4.7 mmol/hg).

EX 3

Replicate Ex 1, but add 0.0012 g of cerium nitrate (Ce($NO_3)_3$) (S. D. Fine) The catalyst is represented as $Rh_1Zn_{0.2}Fe_{0.2}Ce_{0.1}Na_{0.1}-NC_{0.5}/SiO_2$. (Rh: 9.7 mmol/hg; Zn: 3.1 mmol/hg; Fe: 3.6 mmol/hg; Ce: 0.7 mmol/hg; Na: 4.3 mmol/hg; NC: 4.7 mmol/hg).

EX 4

Replicate Ex 3, but substitute 0.0049 g of cobalt nitrate hexahydrate ($Co(NO_3)_2.6H_2O$) (S. D. Fine) for the cerium nitrate. The catalyst is represented as $Rh_1-Zn_{0.2}Fe_{0.2}Co_{0.2}Na_{0.1}-NC_{0.5}/SiO_2$. (Rh: 9.7 mmol/hg; Zn: 3.1 mmol/hg; Fe: 3.6 mmol/hg; Co: 3.4 mmol/hg; Na: 4.3 mmol/hg; NC: 4.7 mmol/hg).

EX 5

Replicate Ex 4, but substitute 0.0038 g of copper nitrate hexahydrate ($Cu(NO_3)_2.6H_2O$ (S. D. Fine) for the $Co(NO_3)_2$ $6H_2O$. The catalyst is represented as $Rh_1-Zn_{0.2}Fe_{0.2}Cu_{0.2}Na_{0.1}NC_{0.5}/SiO_2$. (Rh: 9.7 mmol/hg; Zn: 3.1 mmol/hg; Fe: 3.6 mmol/hg; Cu: 3.1 mmol/hg; Na: 4.3 mmol/hg; NC: 4.7 mmol/hg).

EX 6

Replicate Ex 5, but substitute 0.0049 g of lanthanum nitrate trihydrate ($La(NO_3)_2.3H_2O$) (S. D. Fine) for the $Cu(NO_3)_2.6H_2O$. The catalyst is represented as $Rh_1Zn_{0.2}Fe_{0.2}La_{0.2}Na_{0.1}-NC_{0.5}/SiO_2$. (Rh: 9.7 mmol/hg; Zn: 3.1 mmol/hg; Fe: 3.6 mmol/hg; La: 1.4 mmol/hg; Na: 4.3 mmol/hg; NC: 4.7 mmol/hg).

EX 7

Replicate Ex 5, but substitute 0.0025 g of niobium oxalate hexahydrate ($Nb_2(C_2O_4)_5.2NH_4C_2O_4.6H_2O$ (S. D. Fine) for the $La(NO_3)_2.3H_2O$. The catalyst is represented as $Rh_1Zn_{0.2}Fe_{0.2}Nb_{0.1}Na_{0.1}-NC_{0.5}/SiO_2$. (Rh: 9.7 mmol/hg; Zn: 3.1 mmol/hg; Fe: 3.6 mmol/hg; Nb: 1.1 mmol/hg; Na: 4.3 mmol/hg; NC: 4.7 mmol/hg).

EX 8

Replicate Ex 4, but eliminate $NaNO_3$ and $Na_2CO_3$. The catalyst is represented as $Rh_1Zn_{0.2}Fe_{0.2}Co_{0.2}/SiO_2$. (Rh: 9.7 mmol/hg; Zn: 3.1 mmol/hg; Fe: 3.6 mmol/hg; Co: 3.4 mmol/hg).

EX 9

Replicate Ex 8, substitute 0.5 g MgO for $SiO_2$. The catalyst is represented as $Rh_1Zn_{0.2}Fe_{0.2}Co_{0.2}/MgO$. (Rh: 9.7 mmol/hg; Zn: 3.1 mmol/hg; Fe: 3.6 mmol/hg; Co: 3.4 mmol/hg).

EX 10

Replicate Ex 1, but add 0.0157 g of $Cr(NO_3)_3.9H_2O$, and substitute 0.5 g MgO for $SiO_2$. The catalyst is represented as $Rh_1Zn_{0.2}Fe_{0.2}Cr_{0.5}Na_{0.1}-NC_{0.5}/MgO$. (Rh: 9.7 mmol/hg; Zn: 3.1 mmol/hg; Fe: 3.6 mmol/hg; Cr: 9.6 mmol/hg; Na: 4.3 mmol/hg; NC: 4.7 mmol/hg).

EX 11

Replicate Ex 10, but substitute 0.5 g $MgAl_2O_4$ for MgO. The catalyst is represented as $Rh_1Zn_{0.2}Fe_{0.2}Cr_{0.5}Na_{0.1}-NC_{0.5}/MgAl_2O_4$. (Rh: 9.7 mmol/hg; Zn: 3.1 mmol/hg; Fe: 3.6 mmol/hg; Cr: 9.6 mmol/hg; Na: 4.3 mmol/hg; NC: 4.7 mmol/hg).

EX 12

Replicate Ex 10, but substitute 0.5 g $MgO-Al_2O_3$ for MgO. The catalyst is represented as $Rh_1Zn_{0.2}Fe_{0.2}Cr_{0.5}Na_{0.1}-NC_{0.5}/MgO-Al_2O_3$. (Rh: 9.7 mmol/hg; Zn: 3.1 mmol/hg; Fe: 3.6 mmol/hg; Cr: 9.6 mmol/hg; Na: 4.3 mmol/hg; NC: 4.7 mmol/hg).

EX 13

Replicate Ex 10, but substitute 0.5 g $TiO_2$ for MgO. The catalyst is represented as $Rh_1Zn_{0.2}Fe_{0.2}Cr_{0.5}Na_{0.1}-NC_{0.5}/TiO_2$. (Rh: 9.7 mmol/hg; Zn: 3.1 mmol/hg; Fe: 3.6 mmol/hg; Cr: 9.6 mmol/hg; Na: 4.3 mmol/hg; NC: 4.7 mmol/hg).

EX 14

Replicate Ex 10, but substitute 0.5 g $ZnAl_2O_4$ for MgO. The catalyst is represented as $Rh_1Zn_{0.2}Fe_{0.2}Cr_{0.5}Na_{0.1}-NC_{0.5}/ZnAl_2O_4$. (Rh: 9.7 mmol/hg; Zn: 3.1 mmol/hg; Fe: 3.6 mmol/hg; Cr: 9.6 mmol/hg; Na: 4.3 mmol/hg; NC: 4.7 mmol/hg).

EX 15

Replicate Ex 10, but substitute 0.5 g ZnO for MgO. The catalyst is represented as $Rh_1Zn_{0.2}Fe_{0.2}Cr_{0.5}Na_{0.1}-NC_{0.5}/ZnO$. (Rh: 9.7 mmol/hg; Zn: 3.1 mmol/hg; Fe: 3.6 mmol/hg; Cr: 9.6 mmol/hg; Na: 4.3 mmol/hg; NC: 4.7 mmol/hg).

EX 16

Replicate Ex 10, but substitute 0.5 g $ZnO-Al_2O_3$ for MgO. The catalyst is represented as $Rh_1Zn_{0.2}Fe_{0.2}Cr_{0.5}Na_{0.1}-NC_{0.5}/ZnO-Al_2O_3$. (Rh: 9.7 mmol/hg; Zn: 3.1 mmol/hg; Fe: 3.6 mmol/hg; Cr: 9.6 mmol/hg; Na: 4.3 mmol/hg; NC: 4.7 mmol/hg).

EX 17

Replicate Ex 10, but substitute 0.5 g $ZrO_2-Al_2O_3$ for MgO. The catalyst is represented as $Rh_1Zn_{0.2}Fe_{0.2}Cr_{0.5}Na_{0.1}-NC_{0.5}/ZrO_2-Al_2O_3$. (Rh: 9.7 mmol/hg; Zn: 3.1 mmol/hg; Fe: 3.6 mmol/hg; Cr: 9.6 mmol/hg; Na: 4.3 mmol/hg; NC: 4.7 mmol/hg).

EX 18

Replicate Ex 11, but add 0.0031 g $Mn(NO_3)_2.6H_2O$. The catalyst is represented as $Rh_1Zn_{0.2}Fe_{0.2}Cr_{0.5}Mn_{0.2}Na_{0.1}-NC_{0.5}/MgAl_2O_4$. (Rh: 9.7 mmol/hg; Zn: 3.1 mmol/hg; Fe: 3.6 mmol/hg; Cr: 9.6 mmol/hg; Mn: 3.6 mmol/hg; Na: 4.3 mmol/hg; NC: 4.7 mmol/hg).

EX 19

Replicate Ex 10, but substitute 0.0031 g $Mn(NO_3)_2.6H_2O$ for $Cr(NO_3)_3.9H_2O$. The catalyst is represented as $Rh_1Zn_{0.2}Fe_{0.2}Mn_{0.2}Na_{0.1}-NC_{0.5}/MgO$. (Rh: 9.7 mmol/hg; Zn: 3.1 mmol/hg; Fe: 3.6 mmol/hg; Mn: 3.6 mmol/hg; Na: 4.3 mmol/hg; NC: 4.7 mmol/hg).

EX 20

Replicate Ex 9, but add 0.0031 g $Mg(NO_3)_2.6H_2O$. The catalyst is represented as $Rh_1Zn_{0.2}Fe_{0.2}Co_{0.2}Mg_{0.5}/MgO$ (Rh: 9.7 mmol/hg; Zn: 3.1 mmol/hg; Fe: 3.6 mmol/hg; Co: 3.4 mmol/hg; Mg: 20.6 mmol/hg).

TABLE 1

| Ex. No. | Temperature, °C. | X (Ethylene), % | S (propanal + propanol), % |
|---|---|---|---|
| CEx A | 280 | 11.70 | 57.60 |
| CEx B | 280 | 3.70 | 36.86 |
| Ex 1 | 280 | 7.83 | 63.91 |
| Ex 2 | 280 | 15.91 | 66.84 |
| Ex 3 | 280 | 17.70 | 67.99 |
| Ex 4 | 280 | 32.63 | 69.67 |
| Ex 5 | 280 | 16.68 | 60.46 |
| Ex 6 | 280 | 14.20 | 66.82 |
| Ex 7 | 280 | 15.38 | 53.10 |
| CEx A | 300 | 11.80 | 57.20 |
| CEx B | 300 | 10.07 | 29.96 |
| Ex 1 | 300 | 12.82 | 64.21 |
| Ex 2 | 300 | 24.95 | 66.49 |
| Ex 3 | 300 | 28.02 | 65.89 |
| Ex 4 | 300 | 48.56 | 68.03 |
| Ex 5 | 300 | 26.69 | 58.36 |
| Ex 6 | 300 | 23.26 | 64.63 |
| Ex 7 | 300 | 24.18 | 58.86 |
| CEx A | 320 | 15.00 | 54.10 |
| CEx B | 320 | 19.42 | 25.13 |
| Ex 1 | 320 | 21.75 | 60.38 |
| Ex 2 | 320 | 37.95 | 62.74 |
| Ex 3 | 320 | 42.89 | 62.65 |
| Ex 4 | 320 | 68.03 | 62.83 |
| Ex 5 | 320 | 41.09 | 53.80 |
| Ex 6 | 320 | 35.91 | 60.74 |
| Ex 7 | 320 | 36.97 | 59.28 |
| CEx A | 340 | 14.30 | 51.90 |
| CEx B | 340 | 0.76 | 30.00 |
| Ex 1 | 340 | 30.66 | 54.78 |
| Ex 2 | 340 | 52.28 | 58.51 |
| Ex 3 | 340 | 57.94 | 59.05 |
| Ex 4 | 340 | 78.17 | 59.70 |
| Ex 5 | 340 | 46.09 | 48.52 |
| Ex 6 | 340 | 50.20 | 55.41 |
| Ex 7 | 340 | 51.52 | 53.98 |

Note:
'X' refers to conversion,
'S' refers to selectivity

TABLE 2

| Ex. No. | Temperature, °C. | Pressure, (MPa) | X (Ethylene), % | S (propanal + propanol), % |
|---|---|---|---|---|
| Ex 8 | 280 | 3.5 | 15.44 | 60.95 |
| Ex 8 | 300 | 3.5 | 28.63 | 60.00 |
| Ex 8 | 320 | 3.5 | 45.54 | 52.56 |
| Ex 8 | 340 | 3.5 | 71.77 | 48.18 |
| Ex 8 | 280 | 9.0 | 27.83 | 72.49 |
| Ex 8 | 300 | 9.0 | 46.85 | 69.69 |
| Ex 8 | 340 | 9.0 | 88.74 | 56.97 |
| Ex 9 | 280 | 3.5 | 47.09 | 58.13 |
| Ex 9 | 300 | 3.5 | 47.02 | 56.65 |
| Ex 9 | 320 | 3.5 | 63.72 | 50.52 |
| Ex 9 | 340 | 3.5 | 81.95 | 40.90 |
| Ex. 10 | 280 | 3.5 | 48.37 | 67.18 |
| Ex. 10 | 300 | 3.5 | 50.06 | 67.31 |
| Ex. 10 | 320 | 3.5 | 67.50 | 61.81 |
| Ex. 10 | 340 | 3.5 | 41.88 | 68.28 |
| Ex. 10 | 320 | 9.0 | 65.31 | 71.58 |
| Ex. 10 | 340 | 9.0 | 71.91 | 68.87 |
| Ex. 11 | 280 | 3.5 | 73.06 | 59.28 |
| Ex. 11 | 300 | 3.5 | 81.87 | 54.31 |
| Ex. 11 | 320 | 3.5 | 92.98 | 44.50 |
| Ex. 11 | 340 | 3.5 | 78.78 | 34.72 |
| Ex. 11 | 320 | 9.0 | 96.24 | 47.76 |
| Ex. 11 | 340 | 9.0 | 92.33 | 38.70 |
| Ex. 12 | 280 | 3.5 | 50.51 | 55.80 |
| Ex. 12 | 300 | 3.5 | 71.16 | 47.62 |
| Ex. 12 | 320 | 3.5 | 87.98 | 35.72 |
| Ex. 12 | 340 | 3.5 | 95.60 | 19.98 |
| Ex. 12 | 320 | 9.0 | 95.94 | 33.07 |
| Ex. 12 | 340 | 9.0 | 99.73 | 16.93 |
| Ex. 13 | 280 | 3.5 | 77.96 | 16.17 |
| Ex. 13 | 300 | 3.5 | 96.39 | 9.80 |
| Ex. 13 | 320 | 3.5 | 99.39 | 5.95 |
| Ex. 13 | 340 | 3.5 | 93.39 | 5.92 |
| Ex. 13 | 340 | 9.0 | 99.49 | 6.66 |
| Ex. 14 | 280 | 3.5 | 52.63 | 62.80 |
| Ex. 14 | 300 | 3.5 | 73.87 | 55.70 |
| Ex. 14 | 320 | 3.5 | 92.42 | 41.70 |
| Ex. 14 | 340 | 3.5 | 98.03 | 18.02 |
| Ex. 14 | 320 | 9.0 | 98.38 | 37.73 |
| Ex. 14 | 340 | 9.0 | 99.80 | 18.59 |
| Ex. 15 | 280 | 3.5 | 3.49 | 21.05 |
| Ex. 15 | 300 | 3.5 | 6.00 | 16.04 |
| Ex. 15 | 320 | 3.5 | 10.91 | 9.84 |
| Ex. 15 | 340 | 3.5 | 20.24 | 4.40 |
| Ex. 15 | 320 | 9.0 | 31.06 | 20.24 |
| Ex. 15 | 340 | 9.0 | 46.19 | 13.82 |
| Ex. 16 | 280 | 3.5 | 63.66 | 59.84 |
| Ex. 16 | 300 | 3.5 | 64.99 | 53.97 |
| Ex. 16 | 320 | 3.5 | 90.23 | 44.13 |
| Ex. 16 | 340 | 3.5 | 60.50 | 36.19 |
| Ex. 16 | 320 | 9.0 | 68.06 | 45.97 |
| Ex. 16 | 340 | 9.0 | 87.45 | 38.96 |
| Ex. 17 | 280 | 3.5 | 3.84 | 56.84 |
| Ex. 17 | 300 | 3.5 | 4.51 | 49.67 |
| Ex. 17 | 320 | 3.5 | 9.29 | 42.86 |
| Ex. 17 | 340 | 3.5 | 9.17 | 32.34 |
| Ex. 17 | 320 | 9.0 | 14.45 | 42.97 |
| Ex. 17 | 340 | 9.0 | 21.15 | 35.63 |
| Ex. 18 | 280 | 3.5 | 81.19 | 61.38 |
| Ex. 18 | 300 | 3.5 | 89.30 | 55.10 |
| Ex. 18 | 320 | 3.5 | 98.04 | 45.03 |
| Ex. 18 | 340 | 3.5 | 87.08 | 34.52 |
| Ex. 18 | 320 | 9.0 | 95.95 | 46.41 |
| Ex. 18 | 340 | 9.0 | 96.46 | 38.40 |
| Ex. 19 | 280 | 3.5 | 29.27 | 64.24 |
| Ex. 19 | 300 | 3.5 | 35.37 | 60.27 |
| Ex. 19 | 320 | 3.5 | 45.09 | 55.34 |
| Ex. 19 | 340 | 3.5 | 35.05 | 58.28 |
| Ex. 19 | 320 | 9.0 | 48.88 | 67.29 |
| Ex. 19 | 340 | 9.0 | 56.85 | 64.34 |
| Ex. 20 | 280 | 3.5 | 78.89 | 61.06 |
| Ex. 20 | 300 | 3.5 | 82.67 | 59.88 |
| Ex. 20 | 320 | 3.5 | 95.29 | 54.43 |
| Ex. 20 | 340 | 3.5 | 98.81 | 42.51 |
| Ex. 20 | 280 | 9.0 | 66.31 | 67.86 |
| Ex. 20 | 300 | 9.0 | 89.70 | 63.79 |

Note:
'X' refers to conversion,
'S' refers to selectivity

As seen in Table 1, the present heterogeneous catalyst shown in Ex 1-20 and having a general formula $Rh_aZn_bFe_cX_dY_eO_f$ wherein X=Au, Ce, Co, Cu, La, Mn, Cr and/or Nb, Y=alkali and/or alkaline earth metal produces much better combined selectivity to propanal and propanol and/or higher ethylene conversion compared to the Rh-Alkali (CEx A) or Rh—Zn—Fe-Alkali (CEx B) compositions without other metal promoters.

What is claimed is:
1. A heterogeneous catalyst consisting essentially of a combination of rhodium, zinc, iron, a fourth metal and at least one metal selected from alkali metals and alkaline earth metals on a catalyst support, the combination of metals represented by general formula $Rh_aZn_bFe_cX_dY_eO_f$ wherein X is at least one fourth metal selected from a group consisting of gold, cerium, cobalt, copper, lanthanum, chromium, manganese and niobium, Y is at least one of an alkali metal and an alkaline earth metal, a is a real number within a range of from

0.1 mmol/hg to 50 mmol/hg, b is a real number within a range of from 0.1 mmol/hg to 75 mmol/hg, c is a real number within a range of from 0.1 mmol/hg to 100 mmol/hg, d is a real number within a range of from greater than or equal to 0 mmol/hg to 50 mmol/hg, e is a real number within a range of from greater than or equal to 0 mmol/hg to 1500 mmol/hg, and f is a real number needed to balance the total charges of Rh, Zn, Fe, X and Y elements, provided that d and e cannot both be 0 and when d is greater than 0 and X is at least one of chromium, manganese and niobium, e is also greater than 0, the catalyst support being at least one of silica, alumina, titania, magnesia, zinc aluminate ($ZnAl_2O_4$), magnesium aluminate ($MgAl_2O_4$), magnesia-modified alumina, zinc oxide-modified alumina, zirconium oxide-modified alumina, magnesia-modified silica, zinc oxide-modified silica, and zinc oxide.

2. The catalyst of claim 1, wherein the catalyst is admixed with an amount of an alkali metal carbonate or alkaline earth metal carbonate.

3. The catalyst of claim 2, wherein the carbonate is an alkali metal carbonate and the amount of alkali metal carbonate is within a range of from greater than 0.1 millimole per hectogram to 75 millimole per hectogram based upon combined weight of the heterogeneous catalyst and the alkali metal carbonate.

4. The catalyst of claim 2 wherein the alkali metal carbonate is selected from sodium carbonate and lithium carbonate.

5. A process of converting a feedstream comprising a mixture of carbon monoxide, hydrogen and an alkylene to a product stream that comprises at least one oxygenate that has one carbon atom more than the alkylene, which process comprises placing the feedstream in contact with the catalyst of claim 1 under conditions sufficient to effect conversion of the feedstream to the product stream, said conditions including a temperature within a range of from 100° C. TO 450° C., a pressure within a range of from 12 pounds per square inch gauge (82.7 kilopascals) to 4,000 pounds per square inch gauge (27.6 megapascals), a gas hourly space velocity within a range of from 25 reciprocal hours to 25,000 reciprocal hours, and a feedstream ratio of ethylene to carbon monoxide to hydrogen within a range of from 0.01:10:10 to 10.0:0.01:0.01.

6. The process of claim 5, wherein the alkylene is ethylene and the oxygenate is a three carbon oxygenate selected from propanol and propanal.

\* \* \* \* \*